(12) United States Patent
Hirschel et al.

(10) Patent No.: US 10,376,641 B2
(45) Date of Patent: Aug. 13, 2019

(54) AUTOMATIC INJECTION DEVICE FOR ADMINISTERING A FIXED DOSE

(75) Inventors: Jürg Hirschel, Aarau (CH); Ulrich Moser, Heimiswil (CH); Markus Tschirren, Kirchberg (CH); Patrick Vogt, Niederbipp (CH)

(73) Assignee: TecPharma Licensing AG, Burgdorf (CH)

( * ) Notice: Subject to any disclaimer, the term of this patent is extended or adjusted under 35 U.S.C. 154(b) by 582 days.

(21) Appl. No.: 13/024,970

(22) Filed: Feb. 10, 2011

(65) Prior Publication Data

US 2011/0196339 A1    Aug. 11, 2011

Related U.S. Application Data

(63) Continuation of application No. PCT/CH2009/000267, filed on Jul. 31, 2009.

(30) Foreign Application Priority Data

Aug. 11, 2008    (DE) .......................... 10 2008 037 310

(51) Int. Cl.
*A61M 5/20*    (2006.01)
*A61M 5/32*    (2006.01)

(52) U.S. Cl.
CPC ........... *A61M 5/2033* (2013.01); *A61M 5/326* (2013.01); *A61M 2005/2013* (2013.01); *Y10T 29/49826* (2015.01)

(58) Field of Classification Search
CPC ........ A61M 5/2033; A61M 2005/2013; A61M 2005/208; A61M 2205/581; A61M 2005/3247; A61M 2005/3267; A61M 2005/3268

USPC ....... 604/130, 134–137, 187, 192, 198, 218, 604/220

See application file for complete search history.

(56) References Cited

U.S. PATENT DOCUMENTS

| | | |
|---|---|---|
| 3,742,948 A | 7/1973 | Post |
| 4,902,279 A | 2/1990 | Schmidtz |
| 5,085,641 A | 2/1992 | Sarnoff |
| 5,425,715 A | 6/1995 | Dalling et al. |

(Continued)

FOREIGN PATENT DOCUMENTS

| | | |
|---|---|---|
| CH | 696261 | 3/2007 |
| DE | 19821933 C1 | 11/1999 |

(Continued)

OTHER PUBLICATIONS

Link to Opposition of EP 2323717 https://register.epo.org/application?number=EP09775758&lng=en&tab=doclist, accessed Apr. 11, 2017, 11 pages.

(Continued)

*Primary Examiner* — Kami A Bosworth
(74) *Attorney, Agent, or Firm* — Dorsey & Whitney LLP

(57) ABSTRACT

An injection device for administering a substance, including a housing, a plunger rod which can be moved relative to the housing, at least one retaining element associated with the rod to hold the rod relative to the housing, and a displaceable locking sleeve which can be displaced relative to the housing from one position in which the sleeve holds the at least one retaining element in a retaining position to a second position in which the at least one retaining element is released.

25 Claims, 6 Drawing Sheets

(56) References Cited

U.S. PATENT DOCUMENTS

| | | |
|---|---|---|
| 5,681,291 A | 10/1997 | Galli |
| 5,704,919 A * | 1/1998 | Kraus ............... A61M 25/0631 604/164.11 |
| 6,004,296 A * | 12/1999 | Jansen ................ A61M 5/3135 604/110 |
| 6,099,503 A * | 8/2000 | Stradella ....................... 604/135 |
| 6,203,530 B1 | 3/2001 | Stewart, Sr. |
| 6,387,078 B1 | 5/2002 | Gillespie, III |
| 6,746,429 B2 | 6/2004 | Sadowski et al. |
| 2002/0045866 A1 | 4/2002 | Sadowski et al. |
| 2004/0039337 A1 | 2/2004 | Letzing |
| 2005/0027255 A1* | 2/2005 | Lavi et al. .................... 604/135 |
| 2005/0049559 A1* | 3/2005 | Mathias ............ A61B 5/15003 604/263 |
| 2005/0101919 A1 | 5/2005 | Brunnberg |
| 2005/0203466 A1 | 9/2005 | Hommann |
| 2005/0222539 A1 | 10/2005 | Gonzales |
| 2005/0273054 A1 | 12/2005 | Asch |
| 2005/0277885 A1 | 12/2005 | Scherer |
| 2006/0100588 A1 | 5/2006 | Brunnberg |
| 2006/0264830 A1* | 11/2006 | Hommann .................... 604/136 |
| 2006/0270985 A1 | 11/2006 | Hommann |
| 2007/0021720 A1 | 1/2007 | Guillermo |
| 2007/0112310 A1 | 5/2007 | Lavi |
| 2007/0129686 A1 | 6/2007 | Daily |
| 2007/0167920 A1 | 7/2007 | Hommann |
| 2007/0265568 A1 | 11/2007 | Tsals |
| 2008/0051715 A1 | 2/2008 | Young |
| 2008/0147006 A1 | 6/2008 | Brunnberg et al. |
| 2008/0228147 A1* | 9/2008 | David-Hegerich ... A61M 5/326 604/198 |
| 2008/0262427 A1 | 10/2008 | Hommann |
| 2009/0312705 A1* | 12/2009 | Grunhut .............. A61M 5/2033 604/110 |

FOREIGN PATENT DOCUMENTS

| | | |
|---|---|---|
| DE | 19822031 A1 | 11/1999 |
| DE | 102004060146 | 8/2005 |
| DE | 10 2006 017 209 | 10/2007 |
| DE | 102006038103 | 2/2008 |
| EP | 1932558 | 6/2008 |
| NL | 282268 A | 12/1964 |
| WO | WO 92/19296 A2 | 11/1992 |
| WO | WO 94/11041 A1 | 5/1994 |
| WO | WO 96/32974 A1 | 10/1996 |
| WO | WO 02/47746 A1 | 6/2002 |
| WO | WO 2005/009515 | 2/2005 |
| WO | WO 2005/044344 | 5/2005 |
| WO | WO 2005/070481 | 8/2005 |
| WO | WO 2005/097238 | 10/2005 |
| WO | WO 2005113039 | 12/2005 |
| WO | WO 2006/111862 | 10/2006 |
| WO | WO 2007020090 | 2/2007 |
| WO | WO 2007/131025 | 11/2007 |
| WO | WO 2009/114542 | 9/2009 |
| WO | WO 03/011378 A1 | 2/2013 |

OTHER PUBLICATIONS

International Search Report dated Nov. 6, 2009, for Application No. PCT/CH2009/000267, 6 pages.

International Preliminary Report on Patentability dated Feb. 15, 2011 for Application No. PCT/CH2009/000267, 6 pages.

* cited by examiner

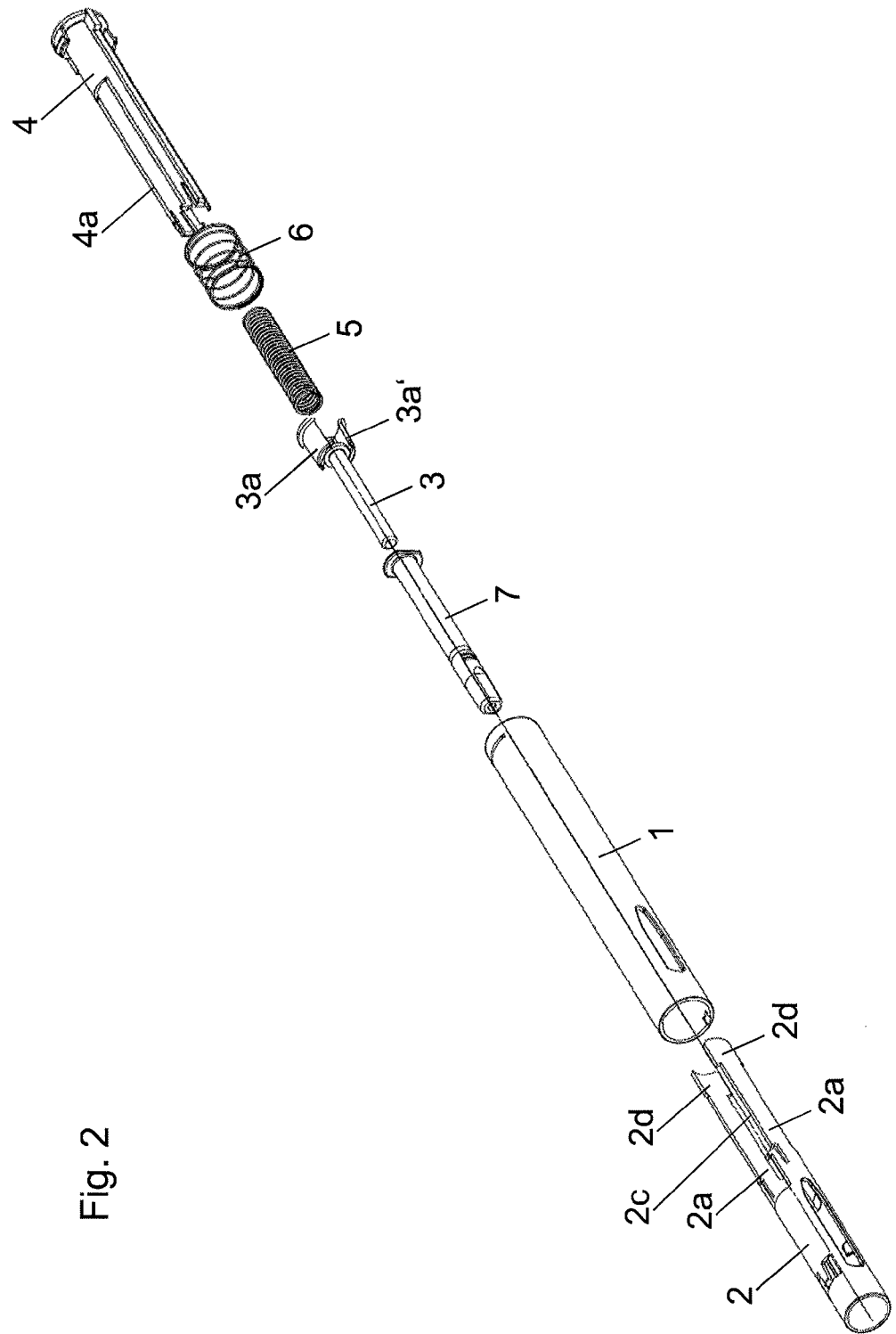

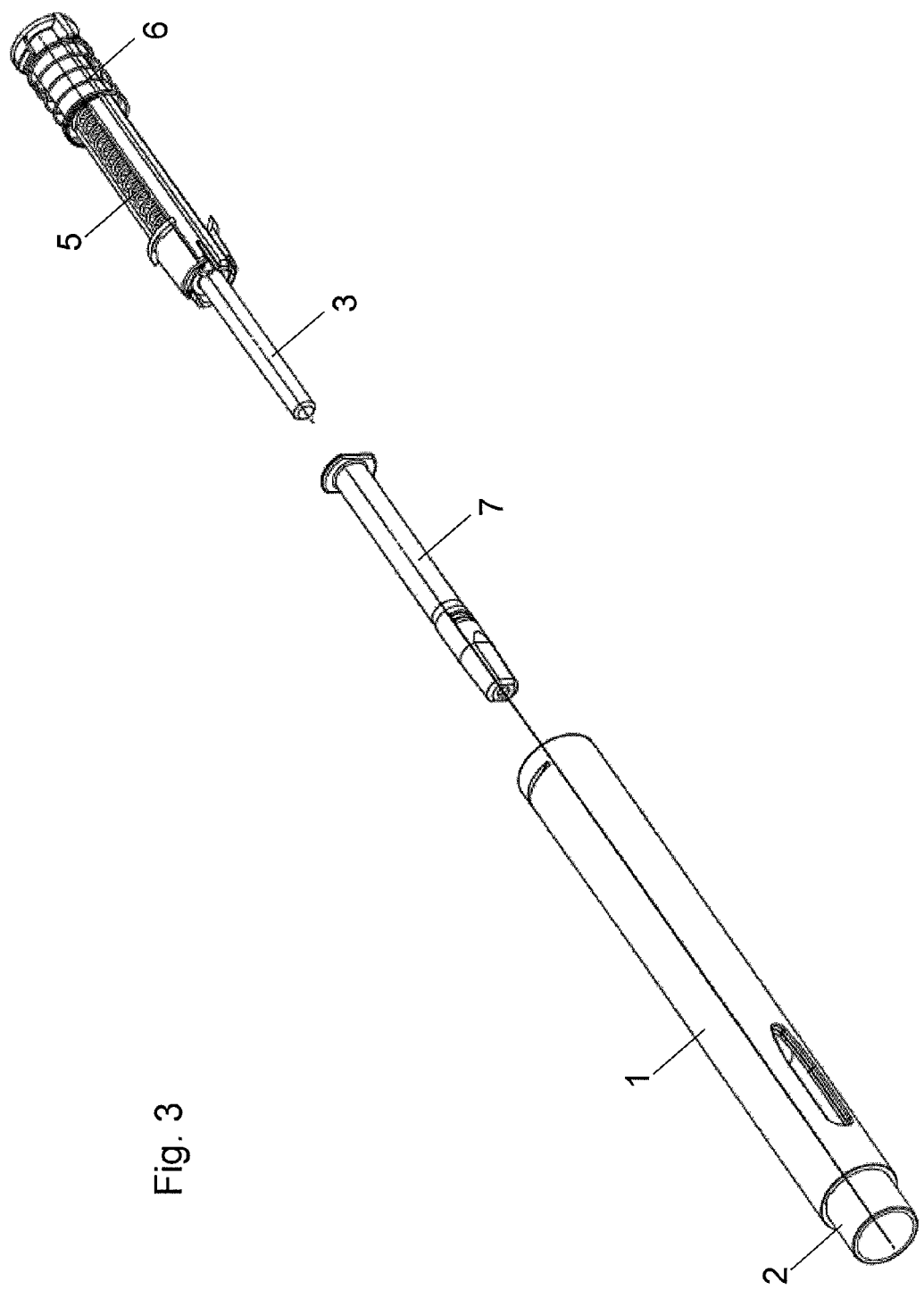

AUTOMATIC INJECTION DEVICE FOR ADMINISTERING A FIXED DOSE

CROSS-REFERENCED RELATED APPLICATIONS

This application is a continuation of International Patent Application No. PCT/CH2009/000267 filed Jul. 31, 2009, which claims priority to German Patent Application No. DE 10 2008 037 310.9 filed Aug. 11, 2008, the entire contents of both of which are incorporated herein by reference.

BACKGROUND

This application relates to devices for injecting, delivering, infusing, administering or dispensing a substance, and to methods of making and using such devices. More particularly, it relates to a device for self-administering a fixed dose of a substance. Such a device may be thought of and referred to as an injection pen, a fixed-dose injection pen or a fixed dose pen, and provides a convenient, efficient way of self-administering a substance stored in an ampoule or syringe inside the injection pen on a one-off basis.

An example of an injection device for administering a fixedly set dose on a one-off basis, wherein the dose can be pre-set, is known from patent specification DE 10 2006 038 103 A1 owned and filed by the owner of the present application.

SUMMARY

An object of the present invention is to provide an injection device for administering a fixed, pre-set quantity of a substance on a one-off basis, wherein the device has a simple design and is easy to operate.

In one embodiment, the present invention comprises an injection device for administering a substance, comprising a housing, a plunger rod which can be moved relative to the housing, at least one retaining element associated with the rod to hold the rod relative to the housing, and a displaceable locking sleeve which can be displaced relative to the housing from one position in which the sleeve holds the at least one retaining element in a retaining position to a second position in which the at least one retaining element is released.

In one embodiment, the present invention comprises an injection device comprising a housing, a plunger rod which can be moved in the housing and on which at least one retaining element is provided that holds the plunger rod relative to the housing, and further comprising a displaceable locking unit, e.g. a cover sleeve, which can be displaced inside the housing, and which in a first position holds the at least one retaining element positively in a retaining position relative to the housing and in a second position releases the at least one retaining element.

In one embodiment, the present invention comprises an injection device having a housing, by which the injection device can be held by a user. A plunger rod is provided inside the housing, which is able to push against a stopper or piston of an ampoule or syringe, likewise disposed inside the injection device, to force out a substance contained inside the ampoule or syringe and administer it by pushing against the stopper, e.g. by a needle. In some embodiments, the plunger rod has at least one retaining element which can be moved or outwardly deflected, for example a resilient arm with a radially projecting locating region. The at least one retaining element holds the plunger rod in a fixed position relative to the housing, in some embodiments on or against the housing, so that it is not able to move. A moving or sliding locking element is also provided on or in the injection device, for example a sleeve, e.g. a protective sleeve, which is able to move relative to the housing and which holds the at least one retaining element in a fixed position relative to the housing when the locking element or sleeve is in a first position. The at least one retaining element can be released when the locking element or sleeve is moved out of the first position so that the coupling between the plunger rod and the injection device or housing is released, and the plunger rod can be moved or pushed inside the injection device to initiate or effect the injection.

In some preferred embodiments, the locking element or sleeve is a protective sleeve located or disposed at or in the distal region (this region may also be thought of and/or referred to as the front, forward or needle region) of the injection device and extending out from the injection device. The protective sleeve can be pushed relative to the injection device or relative to the housing of the injection device, e.g. in an axial direction into the housing of the injection device, if the injection device is placed on or against a surface such as a user's or patient's skin. In some embodiments, the protective sleeve is mounted in the housing of the injection device so that it is prevented from turning. When the housing of the injection device is pushed toward or against the skin, the protective sleeve is moved or pushed into the housing or into the injection device, in some preferred embodiments after overcoming a minimum opposing force caused by a releasable catch connection. In this case, the injection device and/or its housing moves toward the skin surface.

In some preferred embodiments, at least one rib or catch or retaining step is provided on the housing, against which the at least one retaining element can be retained. The rib or retaining step may have a surface to which a longitudinal or axial axis of the injection device extends perpendicularly. In some preferred embodiments, the rib or step may be chamfered so that the at least one retaining element of the plunger rod can be released more easily when it is no longer retained or secured by the displaceable protective sleeve. The at least one retaining element of the plunger rod also has a retaining region, which complements the abutment surface of the retaining step. It can be, thus, likewise slightly chamfered.

In some preferred embodiments, an injection spring element is provided, which is supported on or by the housing or an element fixedly connected or latched to the housing, e.g an end cap. The spring element pushes on the plunger rod in the distal direction (this direction may also be thought of and/or referred to as the forward, injection or delivery direction). In some embodiments, the injection spring element is tensed when the injection device is in the initial position and expends a force which is enough to move the at least one retaining element out of the retaining or locating position when the retaining element is no longer retained or locked by the lock or protective sleeve. As a result, and due to the force of the injection spring element pushing on the plunger rod, the rod is moved relative to the injection device or relative to the housing toward the stopper of the ampoule or syringe to initiate the dispensing process.

In some embodiments, the protective sleeve is locked so that it is not able to rotate in the housing of the injection device or inside the injection device. In some embodiments, it may be locked by an axially extending groove and/or a web of the protective sleeve which co-operates with a co-operating, complementary web and/or an axial groove of the injection device or housing. Such an arrangement may also be thought of and/or referred to as an axial guide.

In some preferred embodiments, a spring is provided which is supported against the injection device or its housing and which pushes on the displaceable protective sleeve so that the protective sleeve spring is able to apply pressure to the protective sleeve in the distal direction. When the injection device is placed on or against a surface and moved toward it, the protective sleeve can be pushed into the injection device against the force of the protective sleeve spring, causing a compression and hence tensing of the protective sleeve spring.

In some embodiments, an ampoule or syringe is provided in the injection device, which is fixedly connected to the housing or fixedly retained in the injection device, for example by one or more stops and/or by the plunger rod pushing against the ampoule or stopper of the ampoule. In some preferred embodiments, the syringe has an injection needle at the distal end, which may be made safe by being covered by a removable needle guard cap. The needle is disposed on or in the injection device so that it is surrounded by the protective sleeve when the latter is pushed out and exposed when the protective sleeve is pushed back, so that when the injection device is pushed onto or against a surface, e.g. the skin, the protective sleeve can be pushed in so that the injection needle, now exposed, can be used to effect the injection. In some embodiments, the injection is effected manually by pushing the injection device onto or against a surface, obviating the need to operate a button or trigger element for the injection process. In this respect, the protective sleeve is mounted in or on the injection device so that when the injection device is pushed onto or against a surface, against or on which the protective sleeve then lies, an initial force must be overcome to enable the protective sleeve to be pushed in. This helps ensures that the injection takes place quickly once the initial force has been overcome and the protective sleeve is pushed back quickly due to the subsequent force, thus enabling a rapid piercing action by the needle.

Another aspect of the present invention is that it relates, in some embodiments, to an injection device which can be assembled from few individual parts, for example only three or four individual parts, which may be molded from a plastic, e.g. a housing, protective sleeve, plunger rod and, optionally, an end cover or cap. In this respect, only a single spring is provided for the injection and, optionally, another spring for the protective sleeve.

In accordance with some preferred embodiments of the present invention, an injection device can be obtained by which it is possible to set a single dose, for being administering once, after which the injection device automatically locks after the administering. Accordingly, the administered or dispensed volume is fixed on a predefined basis, e.g. it may be the entire contents of the ampoule or syringe contained in the injection device. In some preferred embodiments, dispensing takes place automatically after piercing, an advantage of which is that no other operating mechanism needs to be operated to initiate the dispensing operation after piercing. The dispensing operation takes place totally automatically after the piercing operation. In some preferred embodiments, the injection device has a safety needle guard and locks or protects the injection needle after use. In other words, in some embodiments, after n injection has taken place, the protective sleeve is automatically returned or pushed back out in the axial direction beyond the injection needle.

Another aspect of the present invention is that it relates to a method of assembling or fitting an injection device comprising, in some embodiments, at least two or exactly two sub-units, wherein an ampoule or syringe to be inserted in the device is not regarded as a sub-unit. When assembling the injection device from the two sub-units, an injection spring is not tensed until the sub-units are assembled. In some preferred embodiments, the injection spring is an integral part of one of the sub-units and is in the relaxed, non-compressed or non-tensed state when the two sub-units are not assembled. This helps ensure that processes which might cause impairment or alteration due to the pressure expended by a tensed injection spring do not start to occur on assembly of the sub-units.

In some preferred embodiments, one of the two units comprises the housing of the injection device and, optionally, also a protective sleeve which is inserted in the housing, is able to slide relative to it and may extend out from the distal region of the housing. The second sub-unit comprises a plunger rod, an injection spring and an injection spring support element, and the injection spring is tensed between the injection spring support element and plunger rod and can be compressed, for example. The plunger rod or plunger rod element may be moved relative to the injection spring support element and can be pushed into it guided by the injection spring support element, so that the injection spring can be tensed or compressed between the plunger rod and injection spring support element. When the injection device is being assembled, a syringe or ampoule may be inserted between the first sub-unit and the second sub-unit prior to assembly, e.g., pushed into the first sub-unit. The second sub-unit can then be coupled to, inserted in or pushed into the first sub-unit. In this respect, the plunger rod or distal end of the plunger rod is pushed against the syringe or ampoule or against a stopper which is able to slide in the syringe or ampoule. Since no fluid or no substance is able to escape from the ampoule or syringe in the initial state because a needle guard element is fitted and the plunger rod is pushed relative to the injection spring support element due to the pressure of the stopper, as the second sub-unit is inserted in the first sub-unit, the injection spring is tensed. A protective sleeve spring may also optionally be provided between the first and the second sub-unit or on the second sub-unit, which lies between the injection spring support element on the one hand and the protective sleeve on the other hand in the assembled state, so that the protective sleeve causes the protective sleeve spring to tense or compress as it is inserted in the housing.

BRIEF DESCRIPTION OF THE DRAWINGS

FIG. 2 is an exploded view of the injection device illustrated in FIG. 1 prior to assembly;

FIG. 3 shows the injection device illustrated in FIG. 2 in the partially assembled state.

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making embodiments of the invention and/or components thereof may be selected from appropriate materials such as metal, metallic alloys, ceramics, plastics, etc. Unless otherwise indicated specifically or by context, positional terms (e.g., up, down, front, rear, distal, proximal, etc.) are descriptive not limiting. Same reference numbers are used to denote same parts or components.

Figure 1:
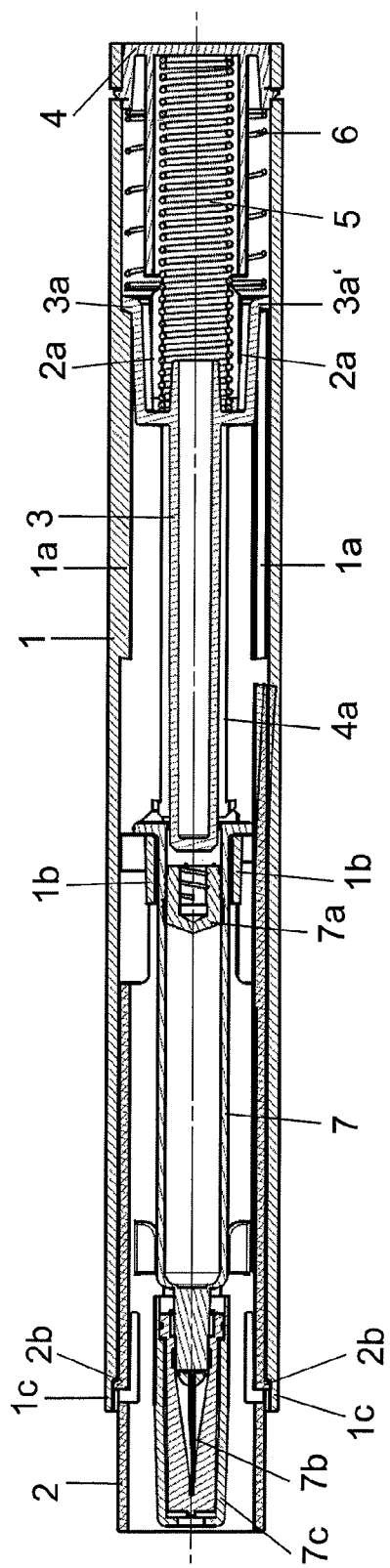
FIG. 1 is a cross-sectional view illustrating an embodiment of an injection device in accordance with the present invention in an initial state.

FIG. 1 illustrates an injection device with a housing 1, which has ribs or webs 1a on its internal face extending in the axial direction. Disposed at a proximal end of the each rib 1a is a respective retaining element 3a in the form of a resilient arm which locates or is urged or biased radially outward. The retaining elements 3a are attached to a plunger rod 3 and retain it in the illustrated axial position. An injection spring 5 is provided in the rear or proximal region of the injection device, which is supported against an end cap 4 latched to or into the housing and which pushes on the plunger rod 3 and pushes the retaining elements 3a of the plunger rod 3 in the distal (forward) direction. The retaining elements 3a of the plunger rod 3 are retained in the locating or retained position on the edges of the webs 1a by arms 2a of a protective sleeve 2, in a positively fitting arrangement or with a slight clearance, so that an injection spring 5 cannot push the plunger rod 3 in the distal direction.

Disposed at the distal end of the plunger rod 3 is an ampoule or syringe 7 with a stopper 7a which is able to slide in it, against which the plunger rod 3 is able to push. Disposed at the distal or front end of the syringe 7 is an injection needle 7b, on which a needle guard cap 7c is fitted, which is removed before using the injection device. The protective sleeve 2 has lugs 2b projecting radially outward in the region of the front or distal half, which locate in a co-operating groove or recess 1c of the housing to generate an initial resistance when the protective sleeve 2 is pushed by a user holding or urging the housing 1 against a surface. As the force applied by the user pushing on the housing 1 in the distal direction becomes stronger, these retaining elements 1c are released from their retaining position and release the protective sleeve so that it can slide axially in the injection device 1 abruptly or in a saccadic movement into the injection device 1, as a result of which the injection device 1 is applied in a saccadic movement to the surface causing it to be pierced by the needle 7b.

A protective sleeve spring 6 is provided in the rear or proximal part of the injection device, which is supported against the housing 1 of the injection device or, as in the depicted exemplary embodiment, against an end cap 4 fitted on or connected to the housing 1 and which pushes against the protective sleeve 2 in the distal direction.

FIG. 2 is an exploded view of the injection device illustrated in FIG. 1, in which the individual components of the injection device described above may be seen. The protective sleeve 2 has two arms 2a pointing in the axial direction with proximal end or retaining regions 2d and a releasing cut-out 2c disposed between the arms 2a axially offset from the retaining regions 2d. The plunger rod 3 has two retaining elements 3a and 3a', which can be moved apart from one another by the retaining regions 2d for example and/or secured to prevent them from being pressed together.

FIG. 3 illustrates the partially assembled individual components with the protective sleeve 2 inserted in the housing 1 and the plunger rod 3, injection spring 5 and end cap 4 assembled to form a unit.

FIGS. 1, 4A, 4B and 4C illustrate an embodiments of an operational sequence which takes place during an injection using the injection device, starting from the state in which it is supplied, illustrated in FIG. 1.

The injection device is primed by the injection spring 5, which is compressed or tensed between the plunger rod 3 and end cap 4. The protective sleeve 2 is mounted or suspended so that it is not able to turn in the housing 1 and is pushed into the front, forward or distal position by the protective sleeve spring 6. The syringe 7 is mounted in the housing 1 against stops or retaining elements 1b, and is additionally guided in the protective sleeve 2 by arms or ribs 2a and secured by webs 4a of the end cap 4. The resilient elements 3a associated with the rod 3 project radially outward, and sit against ribs 1a in the housing 1 and are prevented from being deflected radially inward out of the retaining position by the proximal end 2d of the arms 2a of the protective sleeve 2.

The end cap 4 snap fits or latches into the housing 1. This snap-fit or latched connection is suitable to absorb the forces of the injection spring 5 and protective sleeve spring 6.

Figure 4A:
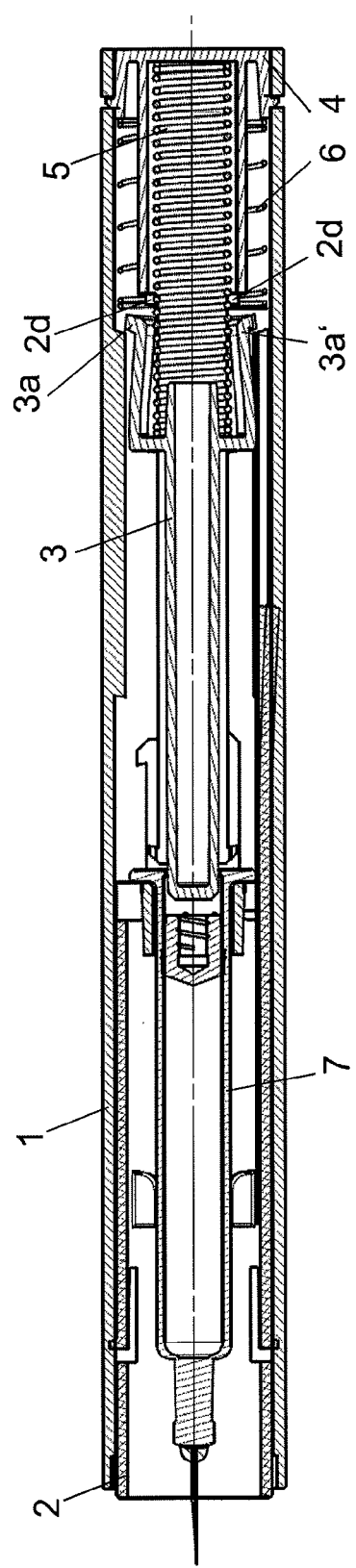
FIGS. 4A to 4C illustrate the sequence which takes placed during an injection using the injection device of FIG. 1.

FIG. 4A illustrates the injection device in a released state after the protective sleeve 7c has been removed from the injection needle 7b. During piercing, the protective sleeve 2 is moved rearwardly toward or into the rear position until the resilient elements 3a of the plunger rod 3 are released and able to deflect or move outwardly via a cut-out 2c in the protective sleeve 2. Due to the chamfer on the ribs 1a in the housing 1 and on the resilient elements 3a of the plunger rod 3, the resilient elements 3a of the plunger rod 3 are deflected outwardly by the force of the injection spring 5 so that the dispensing operation is automatically triggered. The injection spring 5 applies the force which is needed to deflect the resilient elements 3a outward and thus release the plunger rod 3, which is pushed onto the stopper 7a of the syringe 7 by the injection spring 5 pushing it into the syringe 7 and thus automatically triggering the dispensing operation.

The protective sleeve spring 6 lies against the proximal ends 2d of the sleeve 2 and is compressed or tensed by the sleeve 2 as it is inserted.

Figure 4B:
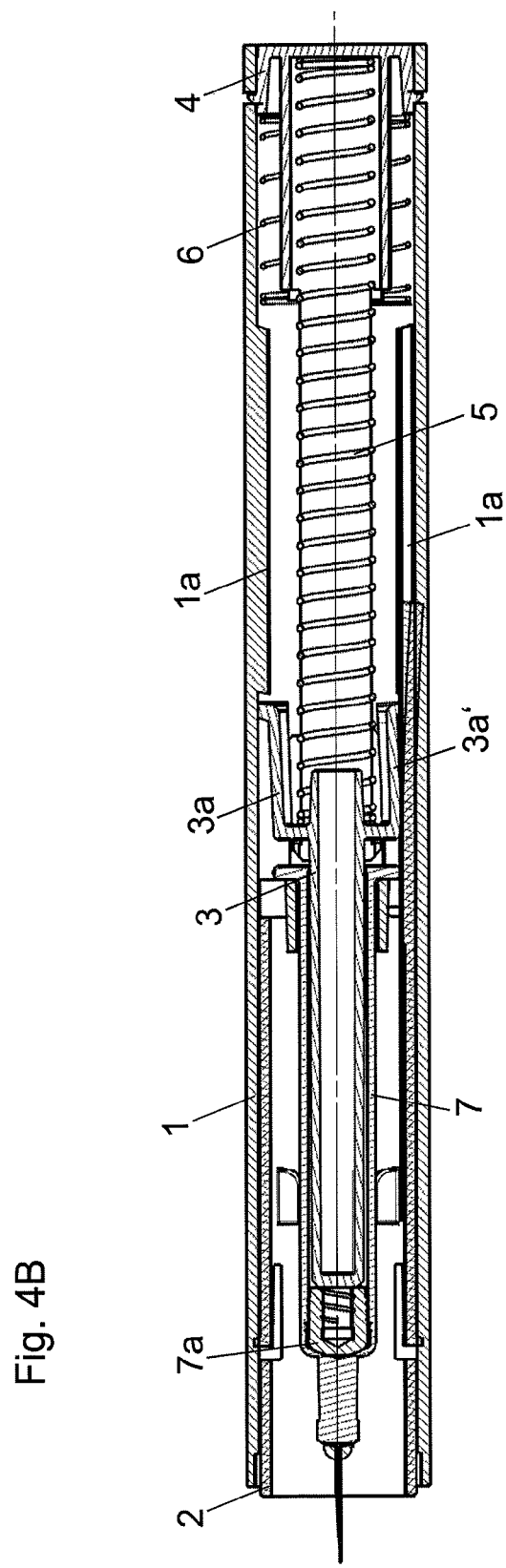

FIG. 4B illustrates the injection device after a dispensing operation. As the injection spring 5 relaxes, the plunger rod 3 is pushed forward in the distal direction. The plunger rod 3 pushes against the stopper 7a of the syringe 7 and empties the syringe 7 completely until the stopper 7a is at the end of the glass body of the syringe 7. The two resilient elements 3a and the plunger rod 3 slide across or along the ribs 1a of the housing 1. At the end of the dispensing operation, one of the two resilient elements 3a snaps over the end of one or more ribs 1a in the housing 1 and causes a noise at the end of the dispensing operation, the so-called "end click," and locks the plunger rod 3 to prevent it from being pushed back.

The other resilient element 3a' on the plunger rod 3 is retained by an arm 2a on the protective sleeve 2 acting as a locking web in the outwardly deflected state.

Figure 4C:
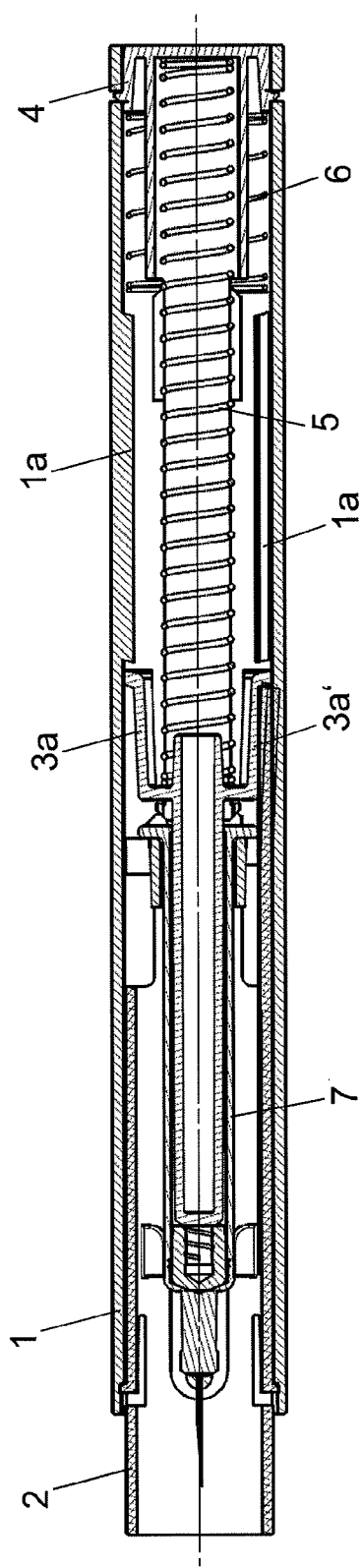

FIG. 4C illustrates the injection device in a locked state after it has been removed from the injection site.

When the injection is terminated, the injection device is removed from the injection site. As this happens, the protective sleeve 2 is pushed into the front-most or distal position by the protective sleeve spring 6. The locking web 2a of the protective sleeve 2 is pushed by the outwardly deflected resilient element 3a' on the plunger rod 3 until the resilient element 3a' snaps over the end of the locking web 2a generating a sound or so-called "click." In this state, the injection device is locked. The protective sleeve 2 can no longer be pushed in because it is blocked by the plunger rod 3, which sits against the three ribs 1a in the housing 1.

Embodiments of the present invention, including preferred embodiments, have been presented for the purpose of illustration and description. They are not intended to be exhaustive or to limit the invention to the precise forms and steps disclosed. The embodiments were chosen and described to illustrate the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection device for administering a substance, comprising:
   a housing;
   a syringe fixedly mounted in the housing;
   a plunger rod;
   at least one retaining element for holding the plunger rod relative to the housing so the rod is not able to move;
   a protective sleeve movable relative to the housing;
   a needle fixedly mounted to the housing and surrounded by the protective sleeve;
   a first spring; and
   a second spring,
   wherein when the protective sleeve is pushed back relative to the housing, against a force of the second spring, from a first position in which the needle is surrounded by the protective sleeve to a second position, the needle is exposed from the protective sleeve,
   wherein when the protective sleeve is pushed against an injection surface, the protective sleeve moves to the second position such that insertion of the needle is effected,
   wherein when the protective sleeve moves from the first position to the second position:
      the at least one retaining element is released and the first spring pushes the plunger rod in a distal direction to initiate a dispensing operation, and
      the second spring is compressed and pushes the protective sleeve in the distal direction,
   wherein a first resilient element snaps in the housing and generates a first click indicating an end of the dispensing operation,
   wherein, upon removal of the injection device from the injection surface and movement of the protective sleeve by the second spring into a front-most position, a second resilient element snaps over an end of a locking element and generates a second click, indicating a locked state of the injection device, and
   wherein in the locked state, the protective sleeve is blocked from moving.

2. The injection device as claimed in claim 1, wherein the protective sleeve has a recess for receiving the at least one retaining element in the second position.

3. The injection device as claimed in claim 1, in which the at least one retaining element is resilient and outwardly biased in a radial direction and comprises at least one retaining region.

4. The injection device as claimed in claim 1, wherein the housing comprises at least one abutment edge against which the at least one retaining element can be supported to prevent the at least one retaining element from sliding in the distal direction in a first position and to prevent the at least one retaining element from sliding in a proximal direction in a second position offset in the distal direction.

5. The injection device as claimed in claim 1, wherein the protective sleeve is mounted in the housing so that the protective sleeve is prevented from rotating.

6. The injection device as claimed in claim 1, wherein the protective sleeve is axially offset from a retaining region which holds the at least one retaining element in the retained position.

7. The injection device as claimed in claim 1, wherein the first spring is an injection spring which is supported against the housing or against an element connected to the housing.

8. The injection device as claimed in claim 1, wherein, in the second position of the protective sleeve, the protective sleeve releases the at least one retaining element to automatically trigger the dispensing operation, and wherein the first resilient element causes the first click at the end of the dispensing operation by interaction with an element of the housing.

9. An injection device for administering a substance, comprising:
   a housing;
   a needle fixedly mounted to the housing;
   a plunger rod;
   at least one retaining element for retaining the plunger rod relative to the housing;
   a displaceable lock comprising a protective sleeve which is able to slide inside the housing and holds the at least one retaining element in a retained position relative to the housing in a first position and which releases the at least one retaining element in a second position;
   a first spring; and
   a second spring,
   wherein when the protective sleeve is pushed back relative to the housing from the first position in which the needle is surrounded by the protective sleeve to the second position, the needle is exposed from the protective sleeve to enable manual insertion of the needle,
   wherein when the protective sleeve moves from the first position to the second position:
      the at least one retaining element releases and the first spring pushes the plunger rod in a distal direction to initiate a dispensing operation,
      the second spring is compressed and pushes the protective sleeve in the distal direction,
   wherein a first resilient element snaps in the housing and generates a first click indicating an end of the dispensing operation,
   wherein, upon removal of the injection device from an injection surface and movement of the protective sleeve by the second spring into a front-most position, a second resilient element snaps over a locking element and generates a second click indicating a locked state of the injection device, and
   wherein in the locked state, the protective sleeve is blocked by the plunger rod from moving.

10. The injection device as claimed in claim 9, in which the at least one retaining element is resilient and outwardly biased in a radial direction and comprises at least one retaining region.

11. The injection device as claimed in claim 9, wherein the housing comprises at least one abutment edge against which the at least one retaining element can be supported to prevent the at least one retaining element from sliding in the distal direction in a first position and to prevent the at least one retaining element from sliding in a proximal direction in a second position offset in the distal direction.

12. The injection device as claimed in claim 9, wherein the protective sleeve is mounted in the housing so that the protective sleeve is prevented from rotating.

13. The injection device as claimed in claim 9, wherein the protective sleeve is axially offset from a retaining region which holds the at least one retaining element in the retained position, and has a recess to release the at least one retaining element after the protective sleeve has moved to the second position.

14. The injection device as claimed in claim 9, wherein the first spring is an injection spring which is supported against the housing or against an element connected to the housing.

15. The injection device as claimed in claim 9, wherein the second spring is a protective sleeve spring which is supported against the housing of the injection device or an element connected to the housing.

16. The injection device as claimed in claim 9, wherein, in the second position of the protective sleeve, the displaceable lock releases the at least one retaining element to automatically trigger the dispensing operation, and wherein the first resilient element causes the first click at the end of the dispensing operation by interaction with an element of the housing.

17. An injection device for administering a substance, comprising
 a housing;
 a syringe, said syringe with a needle fixedly connected to the housing for manual injection by pushing the injection device onto or against a surface, the needle being surrounded by a protective sleeve in a first position of the protective sleeve and exposed from the protective sleeve when the protective sleeve is pushed back to a second position of the protective sleeve;
 a plunger rod;
 at least one retaining element associated with the plunger rod for retaining the plunger rod relative to the housing;
 a displaceable lock comprising the protective sleeve which protective sleeve is able to slide inside the housing and which displaceable lock holds, in the first position of the protective sleeve, the at least one retaining element in a retained position relative to the housing and which releases, in the second position of the protective sleeve, the at least one retaining element; and
 a resilient element which causes a noise at the end of a dispensing operation and locks the plunger rod at the end of the dispensing operation to prevent the plunger rod from being pushed back.

18. The injection device as claimed in claim 17, wherein the at least one retaining element is resilient and biased in a radial direction and comprises at least one retaining region which holds the at least one retaining element in the retained position.

19. The injection device as claimed in claim 18, wherein the protective sleeve is axially offset from the at least one retaining region, and wherein the displaceable lock comprises a recess to release the at least one retaining element after the protective sleeve has moved to the second position.

20. The injection device as claimed in claim 19, further comprising an injection spring which is supported against the housing or against an element connected to the housing and which pushes the plunger rod in a distal direction.

21. The injection device as claimed in claim 20, further comprising a protective sleeve spring which is supported against the housing of the injection device or an element connected to the housing and which pushes the protective sleeve in the distal direction.

22. The injection device as claimed in claim 17, wherein the at least one retaining element is provided on the plunger rod.

23. The injection device as claimed in claim 17, wherein the protective sleeve is mounted in the housing so that the protective sleeve is prevented from rotating.

24. The injection device as claimed in claim 17, wherein, in the second position of the protective sleeve, the displaceable lock releases the at least one retaining element to automatically trigger the dispensing operation.

25. The injection device as claimed in claim 17, wherein the resilient element causes the noise at the end of the dispensing operation by interaction with an element of the housing.

* * * * *